US012649036B2

(12) United States Patent
Peng

(10) Patent No.:  US 12,649,036 B2
(45) Date of Patent:  Jun. 9, 2026

(54) GAS DELIVERY HOSE HOOK, VENTILATOR SUPPORT DEVICE AND RESPIRATORY THERAPY EQUIPMENT

(71) Applicant: Jie Peng, Xinshao County (CN)

(72) Inventor: Jie Peng, Xinshao County (CN)

( * ) Notice: Subject to any disclaimer, the term of this patent is extended or adjusted under 35 U.S.C. 154(b) by 0 days.

(21) Appl. No.: 18/900,786

(22) Filed: Sep. 29, 2024

(65) Prior Publication Data

US 2026/0091184 A1     Apr. 2, 2026

(51) Int. Cl.
*A61M 16/00*          (2006.01)

(52) U.S. Cl.
CPC . *A61M 16/0003* (2014.02); *A61M 2205/0216* (2013.01); *A61M 2209/082* (2013.01); *A61M 2209/084* (2013.01)

(58) Field of Classification Search
CPC ...... A61M 2209/082; A61M 2209/084; A61M 2205/0216; A61M 39/10; A61B 50/20; F16L 3/237; F16L 3/24; F16L 3/01; F16M 11/02; F16M 13/02
See application file for complete search history.

(56) References Cited

U.S. PATENT DOCUMENTS

| | | | | | |
|---|---|---|---|---|---|
| 4,262,872 | A | * | 4/1981 | Kodet | A61G 1/04 |
| | | | | | 5/503.1 |
| 6,292,984 | B1 | * | 9/2001 | Nelson | B60P 7/0823 |
| | | | | | 410/97 |
| D794,434 | S | * | 8/2017 | McCoy | D8/380 |
| 11,473,333 | B2 | * | 10/2022 | Sykes | E04H 17/10 |
| D1,008,010 | S | * | 12/2023 | Huang | D8/367 |
| 2002/0079123 | A1 | * | 6/2002 | Lange | H01R 13/59 |
| | | | | | 174/84 R |
| 2016/0067585 | A1 | * | 3/2016 | Ogle | A63B 71/0619 |
| | | | | | 473/422 |
| 2018/0272086 | A1 | * | 9/2018 | Klinger | A61M 5/1415 |
| 2021/0298971 | A1 | * | 9/2021 | Paul | A61G 7/0503 |
| 2021/0353482 | A1 | * | 11/2021 | Bardo | A61G 10/005 |
| 2022/0313023 | A1 | * | 10/2022 | Lankford | A47J 47/005 |
| 2022/0409970 | A1 | * | 12/2022 | Zorick | A63B 60/22 |

* cited by examiner

*Primary Examiner* — Kendra D Carter
*Assistant Examiner* — Maap Ellabib

(57)          ABSTRACT
The present disclosure discloses a gas delivery hose hook, a ventilator support device and respiratory therapy equipment, wherein the gas delivery hose hook is applied to a gas delivery hose, the surface of the gas delivery hose is provided with a plurality of grooves which are arranged at intervals along the length direction of the gas delivery hose; the gas delivery hose hook comprises a body, a first hook body is connected to the body and provided with a first limit rib, and the first limit rib extends along an extension direction of the first hook body; at least one second hook body is connected to the body and is arranged at intervals with the first hook body, and two opposite surfaces of the second hook body are convexly provided with second limit ribs.

17 Claims, 7 Drawing Sheets

GAS DELIVERY HOSE HOOK, VENTILATOR SUPPORT DEVICE AND RESPIRATORY THERAPY EQUIPMENT

TECHNICAL FIELD

The present disclosure relates to the technical field of medical instruments, in particular to a gas delivery hose hook, a ventilator support device and respiratory therapy equipment.

BACKGROUND

CPAP (Continuous Positive Airway Pressure), which is specially developed and manufactured to prevent some adverse consequences caused by pure oxygen for newborns, is widely used in pediatric departments of hospitals and thus is a necessary medical equipment for hospitals. Generally speaking, CPAP includes a host computer and a gas delivery hose connected to the host computer.

At present, in order to facilitate the treatment and use, the gas delivery hoses of CPAP are all long, and they need to be arranged with auxiliary devices such as hooks to facilitate access during treatment or storage after treatment. However, in practical use, many problems are often caused by the long gas delivery hose. For example, when the gas delivery hose is wound for many turns, the ventilation is not smooth, or after being placed for a single turn, the gas delivery hose slides down under the gravity of the remaining sections, which affects the placement and use.

SUMMARY

The main object of the present disclosure is to provide a gas delivery hose hook, aiming at improving the smoothness of gas delivery of the gas delivery hose while facilitating the arrangement and storage of the gas delivery hose.

In order to achieve the above object, the gas delivery hose hook provided by the present disclosure is applied to a gas delivery hose, wherein a surface of the gas delivery hose is provided with a plurality of grooves which are arranged at intervals along a length direction of the gas delivery hose; wherein the gas delivery hose hook includes:

a body;

a first hook body connected to the body and provided with a first limit rib, wherein the first limit rib extends along an extending direction of the first hook body; and at least one second hook body is connected to the body and arranged at intervals with the first hook body, wherein two opposite surfaces of the second hook body are convexly provided with second limit ribs;

wherein the gas delivery hose is wound around the first hook body and the second hook body, and the first limit rib and the second limit rib can be embedded in any of the grooves.

In an alternative embodiment, the cross sections of the first limit rib and the second limit rib are rectangular.

In an alternative embodiment, two opposite sides of the second hook body are provided with sliding mounting grooves, the edges of the body are embedded in the sliding mounting grooves, and the second hook body can reciprocate relative to the first hook body.

In an alternative embodiment, the body includes a mounting plate and an elastic anti-slip layer; the first hook body and the second hook body are connected to the mounting plate, the elastic anti-slip layer is connected to two opposite sides of the mounting plate and extends along a length direction thereof; and the elastic anti-slip layer elastically abuts against a groove side wall of the sliding mounting groove.

In an alternative embodiment, the second hook body includes a mounting seat and a hook plate, and the mounting seat is provided with the sliding mounting groove; the second limit ribs are arranged at two opposite sides of the hook plate, and the hook plate is detachably connected to the mounting seat.

In an alternative embodiment, the mounting seat is provided with a clamping groove, the clamping groove penetrates through two opposite side surfaces of the mounting seat, and the hook plate is slidably embedded in the clamping groove.

In an alternative embodiment, the gas delivery hose hook includes a plurality of second hook body bodies, and the plurality of second hook body bodies are connected to the body and arranged at intervals with the first hook body.

The present disclosure further provides a ventilator support device, including a support tray, a mounting structure and a gas delivery hose hook, wherein the gas delivery hose hook is above the gas delivery hose hook;

the support tray is formed with an accommodating groove for accommodating a ventilator, the mounting structure is detachably connected to the support tray, and the gas delivery hose hook is connected to an end of the mounting structure far away from the support tray.

In an alternative embodiment, the mounting structure includes a connecting seat and a mounting rod; the support tray is provided with a plurality of mounting holes, and the connecting seat can be inserted into any of the mounting holes; the mounting rod is connected to the connecting seat, and the gas delivery hose hook is connected to an end of the mounting rod; and the mounting rod can move relative to the support tray, so that the gas delivery hose hook can be in storage state or a use state.

In an alternative embodiment, the mounting structure includes a mounting shaft, the connecting seat is provided with a first shaft hole, and the mounting rod is provided with a second shaft hole; the mounting shaft penetrates through the first shaft hole and the second shaft hole to connect the mounting rod and the connecting seat.

In an alternative embodiment, the mounting structure further includes a fixed buckle, which is connected to the support tray; the gas delivery hose hook is in the storage state, and the middle part of the mounting rod is clamped with the fixed buckle.

In an alternative embodiment, the mounting rod includes a fixed rod body and a movable rod body; the fixed rod body is connected to the connecting seat and is provided with an insertion hole, and the movable rod body is slidably inserted into the insertion hole; and the gas delivery hose hook is connected to an end of the movable rod body.

In an alternative embodiment, the mounting rod further includes a fixed spring, and the fixed spring elastically abuts against the fixed rod body and the connecting seat.

In an alternative embodiment, the mounting rod further includes a fastener, and the fastener is connected to the fixed rod body and the movable rod body.

In an alternative embodiment, the fastener includes an adjusting nut and an elastic snap ring, the elastic snap ring is sleeved outside the movable rod body, and the adjusting nut is sleeved outside the elastic snap ring and is in threaded connection with the fixed rod body; the adjusting nut rotates relative to the fixed rod body so that the elastic snap ring elastically abuts against the adjusting nut and the movable rod body.

In an alternative embodiment, the ventilator support device further includes an elastic fixing rope, one end of which is connected to one side of the support tray, and the other end of which is detachably connected to the other side of the support tray, so as to press the ventilator in the accommodating groove.

In an alternative embodiment, the ventilator support device further includes a fixing hook, the support tray is provided with a fixing hole, and the fixing hook is connected to the end of the elastic fixing rope and can be buckled in the fixing hole.

In an alternative embodiment, the support tray further includes a booster flange, and the booster flange is connected to two opposite sides of the support tray.

In an alternative embodiment, the ventilator support device further includes a fixed suction cup, and the fixed suction cup is connected to the bottom of the support tray.

The present disclosure further provides respiratory therapy equipment, including a ventilator and a ventilator support device, wherein the ventilator support device is the above ventilator support device; the ventilator includes a host machine and a gas delivery hose connected to the host machine; the ventilator support device includes a support tray, a mounting structure and a gas delivery hose hook, the support tray is formed with an accommodating groove, and the host machine part is accommodated in the accommodating groove; the mounting structure is detachably connected to the support tray, the gas delivery hose hook is connected to an end of the mounting structure far away from the support tray, and the gas delivery hose hook is wound around the gas delivery hose hook.

The gas delivery hose hook of the present disclosure is applied to the gas delivery hose, the surface of the gas delivery hose is provided with a plurality of grooves which are arranged at intervals along the length direction of the gas delivery hose, and the gas delivery hose hook includes a body, wherein a first hook body is connected to the body and provided with a first limit rib which extends along the extension direction of the first hook body, at least one second hook body is connected to the body and arranged at intervals with the first hook body, and two opposite surfaces of the second hook body are convexly provided with second limit ribs. In practical use, the gas delivery hose can be repeatedly wound on the first hook body and the second hook body, that is, by arranging the second hook bodies arranged at intervals, the length of the wound gas delivery hose is not only increased to a certain extent, so that the problem that the gas delivery hose is blocked after being stacked for multiple times can be avoided, and the gas delivery is smoother. At the same time, when the gas delivery hose is wound around the first hook body and the second hook body, the first limit rib and the second limit rib arranged on the surface of the gas delivery hose can be clamped in the groove of the gas delivery hose can be clamped in the groove of the gas delivery hose, so that the gas delivery hose is placed more stably, and it is convenient to arrange and store the gas delivery hose.

BRIEF DESCRIPTION OF DRAWINGS

In order to explain the embodiments of the present disclosure or the technical solution in the prior art more clearly, the drawings needed to be used in the description of the embodiments or the prior art will be briefly introduced below. Obviously, the drawings in the following description are only some embodiments of the present disclosure, and other drawings can be obtained according to the structures shown in these drawings without creative work for those skilled in the art.

Figure 1:
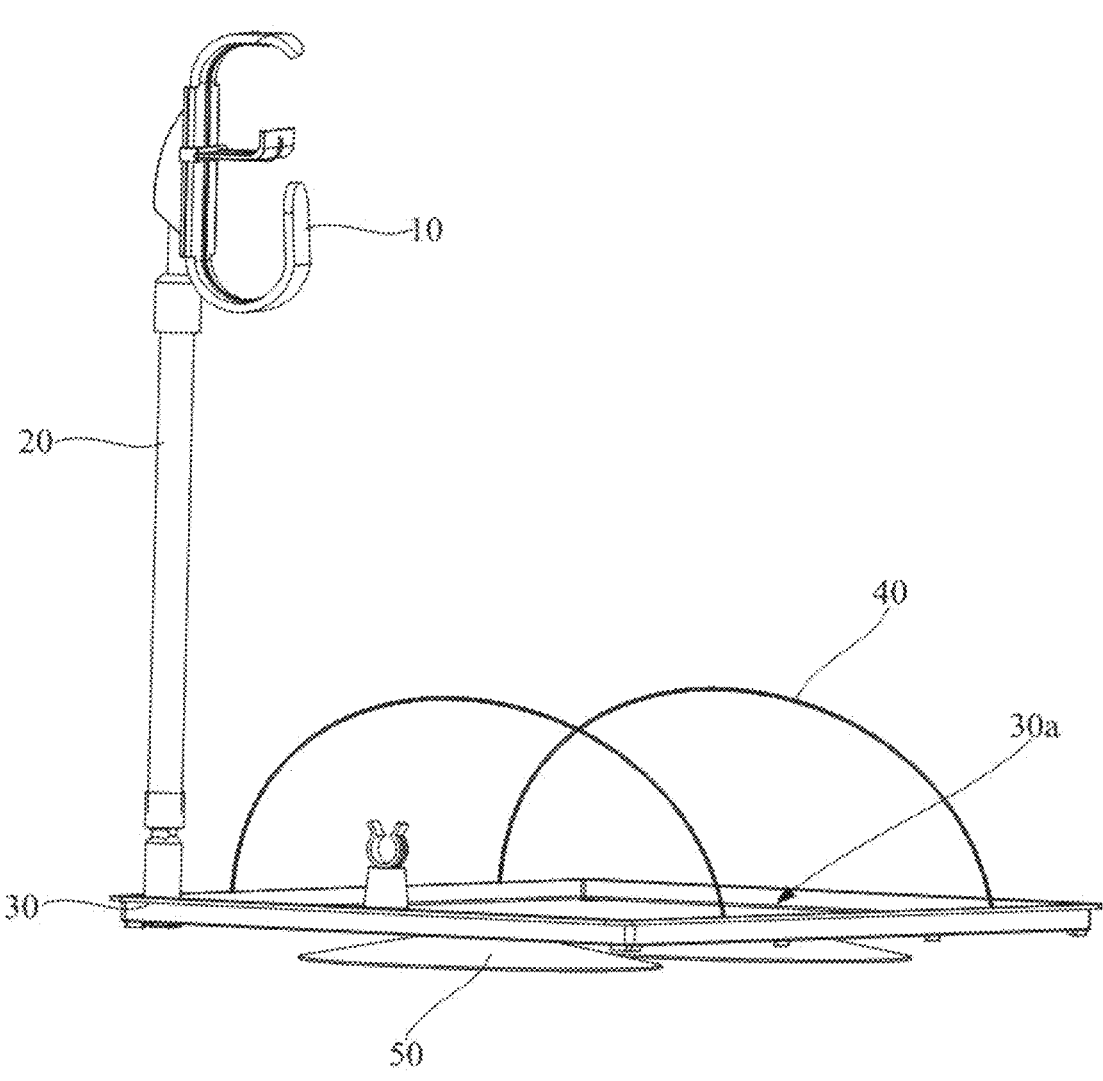
FIG. 1 is a structural schematic diagram of a ventilator support device according to an embodiment of the present disclosure.

| Reference signs in the figures: | | | |
|---|---|---|---|
| Reference sign | Name | Reference sign | Name |
| 100 | Ventilator support device | 22 | Mounting rod |
| 10 | Gas delivery hose hook | 22a | Second shaft hole |
| 11 | First hook body | 221 | Fixed rod body |
| 111 | First limit rib | 222 | Movable rod body |
| twelve | Second hook body | 223 | Fastener |
| 121 | Second limit rib | 2231 | Adjusting nut |
| 122 | Hook plate | 2232 | Elastic snap ring |
| 123 | Mounting seat | 23 | Fixed buckle |
| 123a | Sliding mounting groove | 30 | Support tray |
| 123b | Clamping groove | 30a | Accommodating groove |
| 13 | Body | 30b | Mounting hole |
| 131 | Mounting plate | 31 | Booster flange |
| 132 | Elastic anti-slip layer | 40 | Elastic fixing rope |
| twenty | Mounting structure | 50 | Fixed suction cup |
| 21 | Connecting seat | 200 | Gas delivery hose |
| 21a | First shaft hole | | |

The implementation, functional characteristics and advantages of the present disclosure will be further described with reference to the drawings in combination with embodiments.

DESCRIPTION OF EMBODIMENTS

In the following, the technical solution in the embodiment of the present disclosure will be clearly and completely described with reference to the attached drawings. Obviously, the described embodiment is only a part of the embodiment of the present disclosure, but not the whole embodiment. Based on the embodiments in the present disclosure, all other embodiments obtained by ordinary technicians in the field without creative work belong to the scope of protection of the present disclosure.

It should be noted that all directional indications (such as up, down, left, right, front, back, etc.) in the embodiment of the present disclosure are only used to explain the relative position relationship and movement situation among components in a certain posture (as shown in the figures), and if the certain posture changes, the directional indications will also change accordingly.

In addition, the descriptions of "first" and "second" in the present disclosure are only used for descriptive purposes, and cannot be understood as indicating or implying their relative importance or implicitly indicating the number of indicated technical features. Therefore, the features defined as "first" and "second" can explicitly or implicitly include at least one of these features. In addition, the technical solutions of each embodiment can be combined with each other, but they must be based on the realization of ordinary technicians in the field. When the combination of technical solutions is contradictory or impossible, it should be considered that the combination of technical solutions does not exist and is not within the scope of protection required by the present disclosure.

Referring to FIGS. 1 to 6, the present disclosure provides a gas delivery hose hook 10.

In the embodiment of the present disclosure, the gas delivery hose hook 10 is applied to a gas delivery hose 200, and the surface of the gas delivery hose 200 is provided with a plurality of grooves which are arranged at intervals along the length direction of the gas delivery hose 200. The gas delivery hose hook 10 includes a body 13; a first hook body 11 connected to the body 13 and provided with a first limit rib 111, wherein the first limit rib 111 extends along an extending direction of the first hook body 11; and at least one second hook body 12 is connected to the body 13 and arranged at intervals with the first hook body 11, wherein two opposite surfaces of the second hook body 12 are convexly provided with second limit ribs 121; wherein the second hook body is provided with a vertical groove on a horizontal axis of the second hook body facing the body;

wherein the vertical groove is configured to correspond to the first limit rib to enable stable engagement between the second hook body and the body; wherein the gas delivery hose 200 is wound around the first hook body 11 and the second hook body 12, and the first limit rib 111 and the second limit rib 121 can be embedded in any of the grooves.

Specifically, the gas delivery hose 200 in this application is used to place and fix the gas delivery hose 200 so as to avoid its disorderly arrangement, wherein the gas delivery hose 200 is made of plastic material and extends in a long strip shape by extrusion process, and a plurality of grooves with rectangular cross sections are formed on the surface thereof.

The body 13 and the first hook body 11 can be integrally formed of plastic or metal materials. The first hook body 11 is connected to the lower part of the body 13 and can extend in an arc shape to better adapt to the shape of the gas delivery hose 200. Of course, the extension shape of the first hook body 11 can also be rectangular or other polygonal structures, which is not specifically limited here. The first limit rib 111 is formed on the inner side of the first hook body 11 and extends along its extension direction. In this application, the first limit rib 111 can extend to one side of the body 13, which not only can better limit and fix the gas delivery hose 200, but also can strengthen the overall strength of the gas delivery hose hook 10 to a certain extent, so as to improve its service life.

In practical use, the gas delivery hose 200 can be repeatedly wound around the first hook body 11 and the second hook body 12, that is, by arranging the second hook bodies 12 arranged at intervals, the length of the wound gas delivery hose 200 is increased to a certain extent, so that the problem that the gas delivery hose 200 is blocked after being stacked for multiple times can be avoided, and the gas delivery can be smoother. At the same time, when the gas delivery hose 200 is wound around the first hook body 11 and the second hook body 12, the first limit rib 111 and the second limit rib 121 arranged on the surface of the gas delivery hose 200 can be clamped in the groove of the gas delivery hose 200, so that the gas delivery hose 200 can be placed more stably, and it is convenient to arrange and store it.

Figure 7:
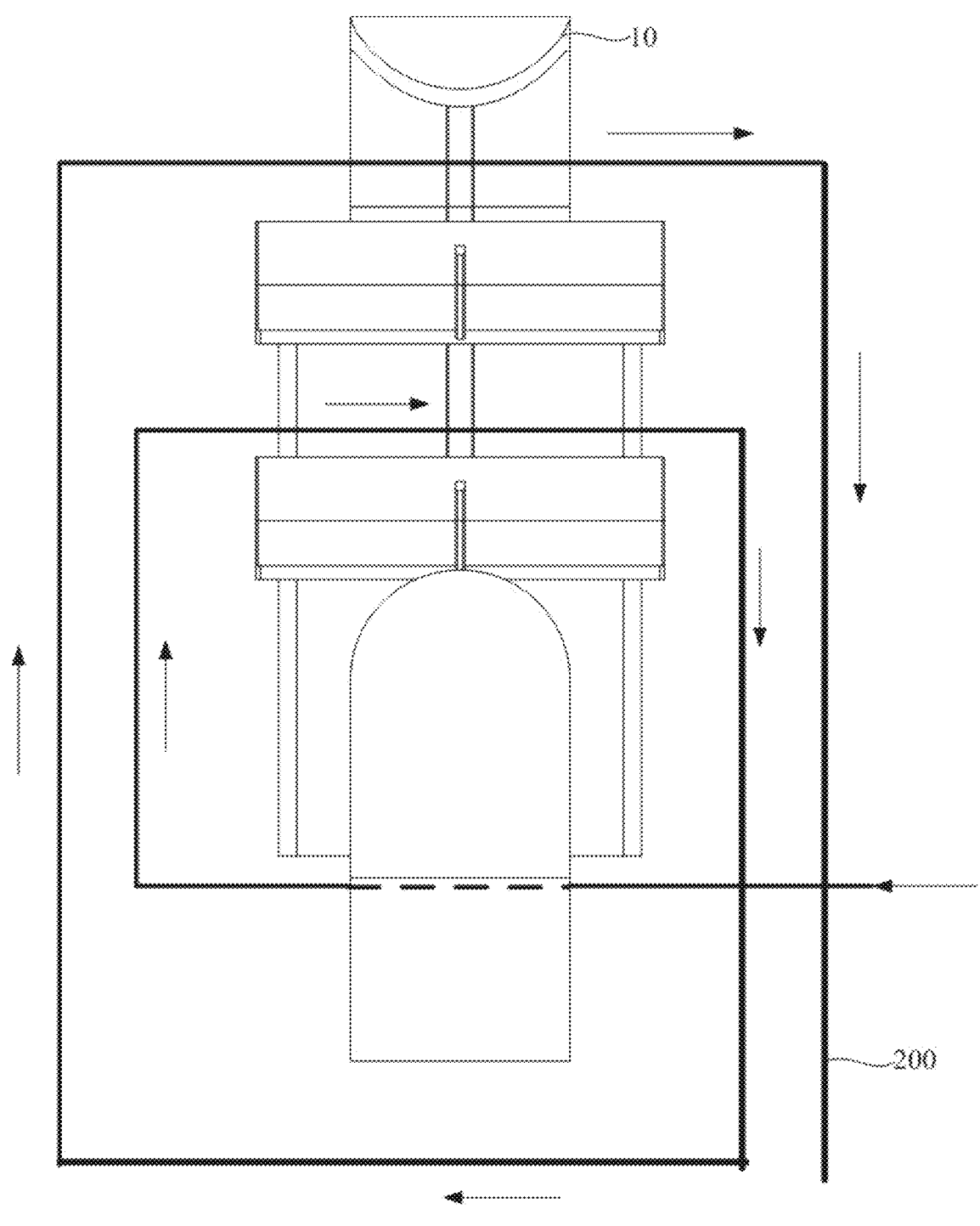
FIG. 7 is a schematic structural view of the gas delivery hose hook shown in FIG. 6 applied to the gas delivery hose.

Please refer to FIG. 7, in this application, the gas delivery hose hook 10 includes a plurality of second hook bodies 12, which are connected to the body 13 and arranged at intervals from the first hook body 11, that is, the second hook bodies 12 and the first hook bodies 11 are arranged at intervals from top to bottom. The arrow direction in the figure is the winding direction of the gas delivery hose 200. It can be seen from the FIG. that by appropriately increasing the number of the second hook bodies 12, the winding of the gas delivery hose 200 can be more reasonable, and the problem that the gas delivery hose 200 is blocked after being stacked for more than one turn can be avoided to a great extent. Moreover, the multi-turn gas delivery hose 200 is hung on the surface of the second hook bodies 12, and its friction is increased, so that the problem that the gas delivery hose 200 slips can be further avoided. The number and spacing of the second hook bodies 12 can be set according to actual needs, and are not specifically limited here.

In the present disclosure, the cross sections of the first limit rib 111 and the second limit rib 121 are rectangular. Generally speaking, the cross section of the groove of the commercially available gas delivery hose 200 is rectangular, therefore in this application, the first limit rib 111 and the second limit rib 121 are set to be rectangular to better fit the groove side wall of the groove, thereby increasing the stability of the gas delivery hose 200. Of course, the cross sections of the first limit rib 111 and the second limit rib 121 can also be semicircular, tapered, etc., and are not specifically limited here.

In an embodiment of the present disclosure, two opposite sides of the second hook body 12 are provided with sliding mounting grooves 123a, and the edges of the body 13 are embedded in the sliding mounting grooves 123a, wherein the distance between the two sliding mounting grooves 123a should be slightly smaller than the width of the body 13, so that the second hook body 12 can be firmly clamped to the body 13 and can reciprocate relative to the first hook body 11 under the action of external force. That is, the distance between the second hook bodies 12 and the first hook bodies 11 can be adjusted according to actual needs, so that the gas delivery hose hook 10 can better adapt to gas delivery hoses 200 with different diameters, and its compatibility and practicability are better.

Further, the body 13 includes a mounting plate 131 and an elastic anti-slip layer 132, wherein the mounting plate 131 is made of a plastic material, the elastic anti-slip layer 132 is made of silica gel or a rubber material, and can be connected to two opposite sides of the mounting plate 131 by integral molding or glue bonding, and the elastic anti-slip layer 132 extends along the length direction of the mounting plate 131. When the second hook body 12 is clamped to the mounting plate 131 through the sliding mounting groove 123a, the elastic anti-slip layer 132 elastically abuts against the groove side wall of the sliding mounting groove 123a. By arranging the elastic anti-slip layer 132, on the one hand, the connection between the second hook body 12 and the mounting plate 131 can be more stable through its elastic force, and it is not easy to slide when placing the gas delivery hose 200. On the other hand, when the user moves the second hook body 12, the elastic anti-slip layer 132 can protect the mounting plate 131 to a certain extent, so as to prevent it from being excessively worn during use, which will affect the use effect.

Figure 5:
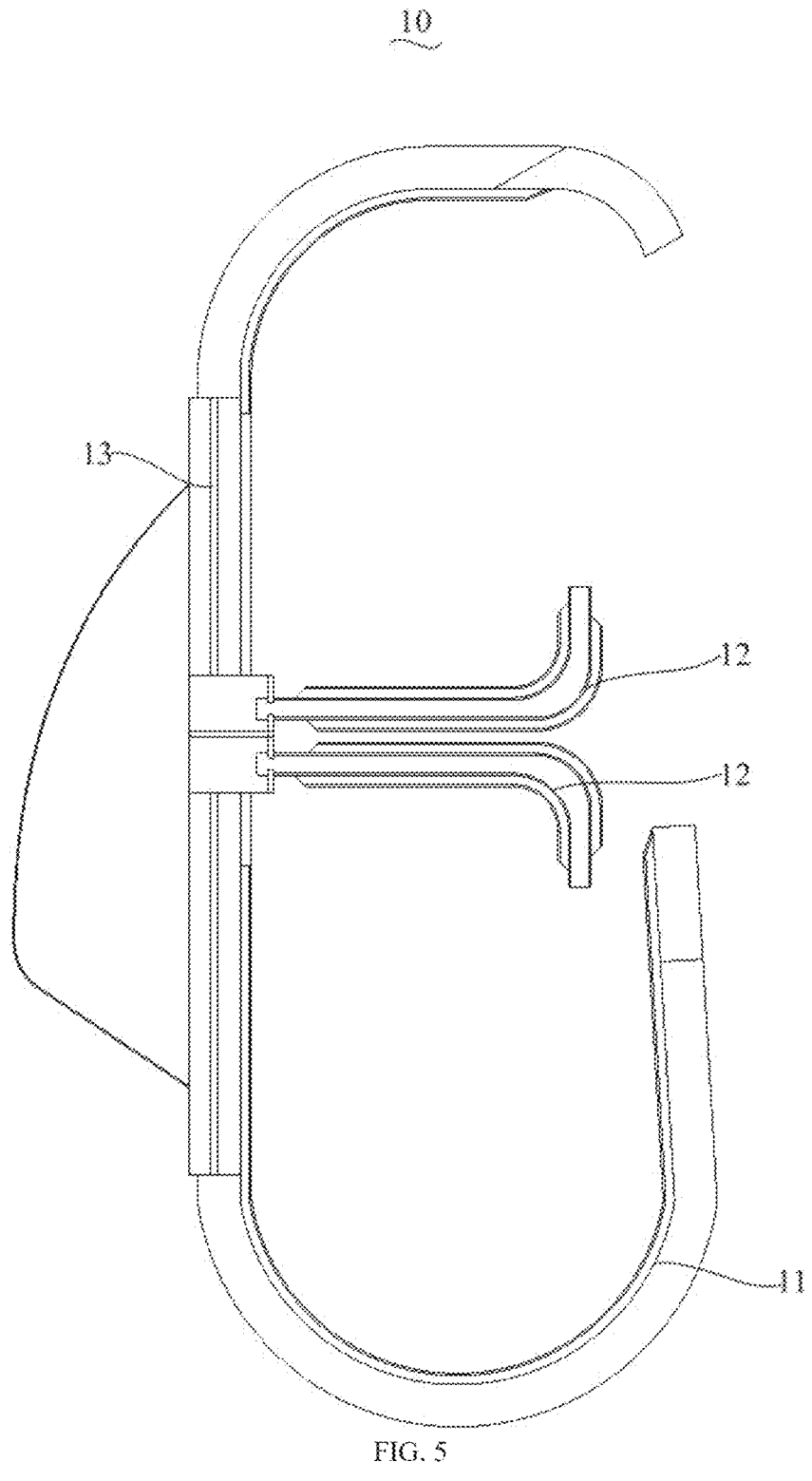
FIG. 5 is a side view of another embodiment of the gas delivery hose hook shown in FIG. 4.
Figure 6:
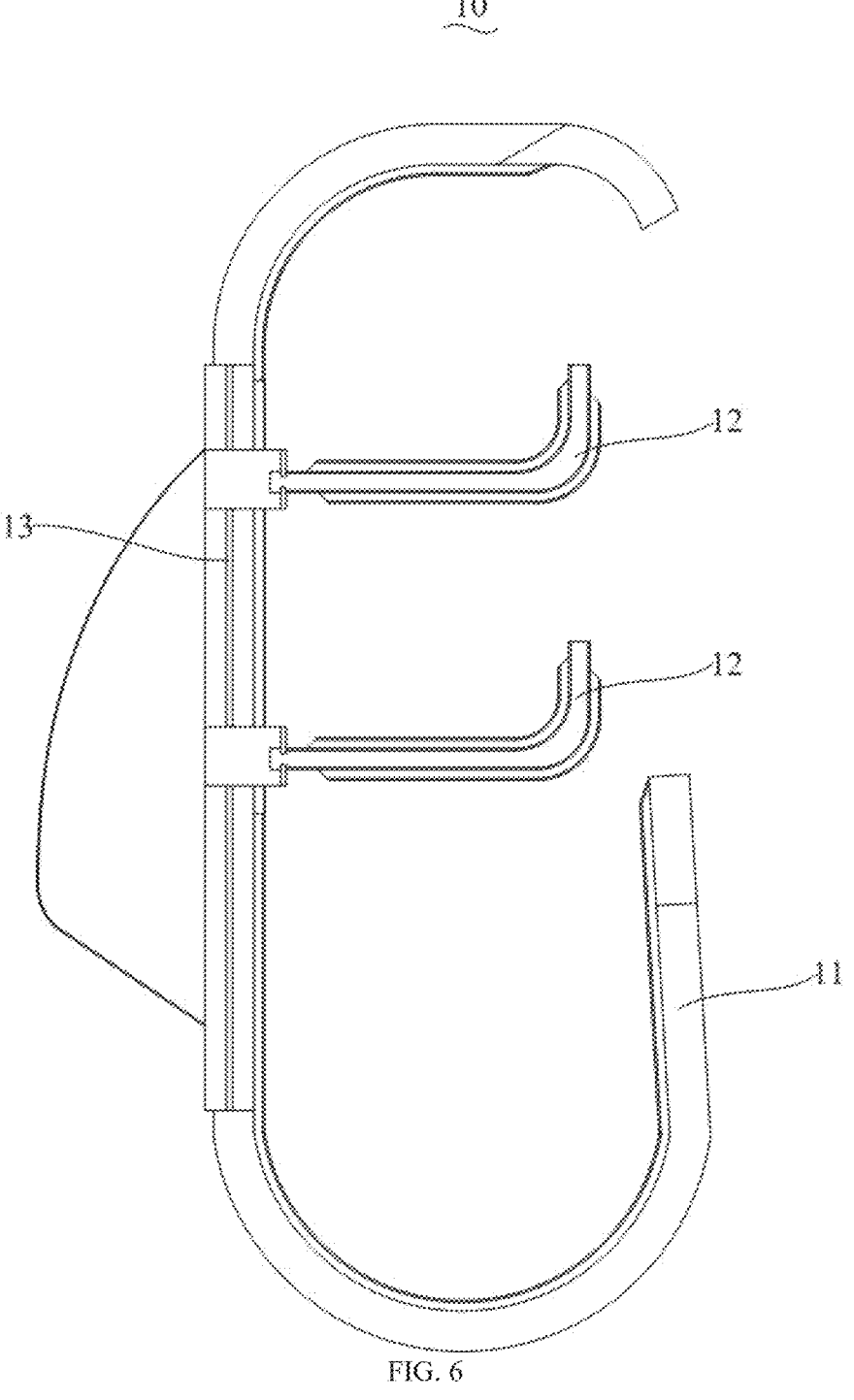
FIG. 6 is a side view of another embodiment of the gas delivery hose hook shown in FIG. 4.

Please refer to FIG. 5 and FIG. 6 again. In this embodiment, the second hook body 12 includes a detachably connected mounting seat 123 and a hook plate 122, wherein the mounting seat 123 is slidably connected with the mounting plate 131 through a sliding mounting groove 123a, and the second limit ribs 121 are arranged at two opposite sides of the hook plate 122. Specifically, the mounting base 123 is provided with a clamping groove 123b, which is a T-shaped groove. The clamping groove 123b passes through two opposite side surfaces of the mounting base 123, and the end of the hook plate 122 is formed with a clamping protrusion (not shown) which is suitable for the shape of the clamping groove 123b, and the clamping protrusion can be slidably inserted into the clamping groove 123 on the two opposite side surfaces of the mounting base 123 to connect the hook plate 122 with the mounting seat 123. In this application, the hook plate 122 and the mounting seat 123 are detached and connected, so that it is convenient for users to adjust the orientation of the hook plate 122 according to actual needs, so as to better adapt to the use needs under different environmental conditions. The hook plate 122 slides on the side of the mounting seat 123 and is clamped in the clamping groove 123b, and its mounting and disassembly are simpler and more labor-saving.

Figure 2:
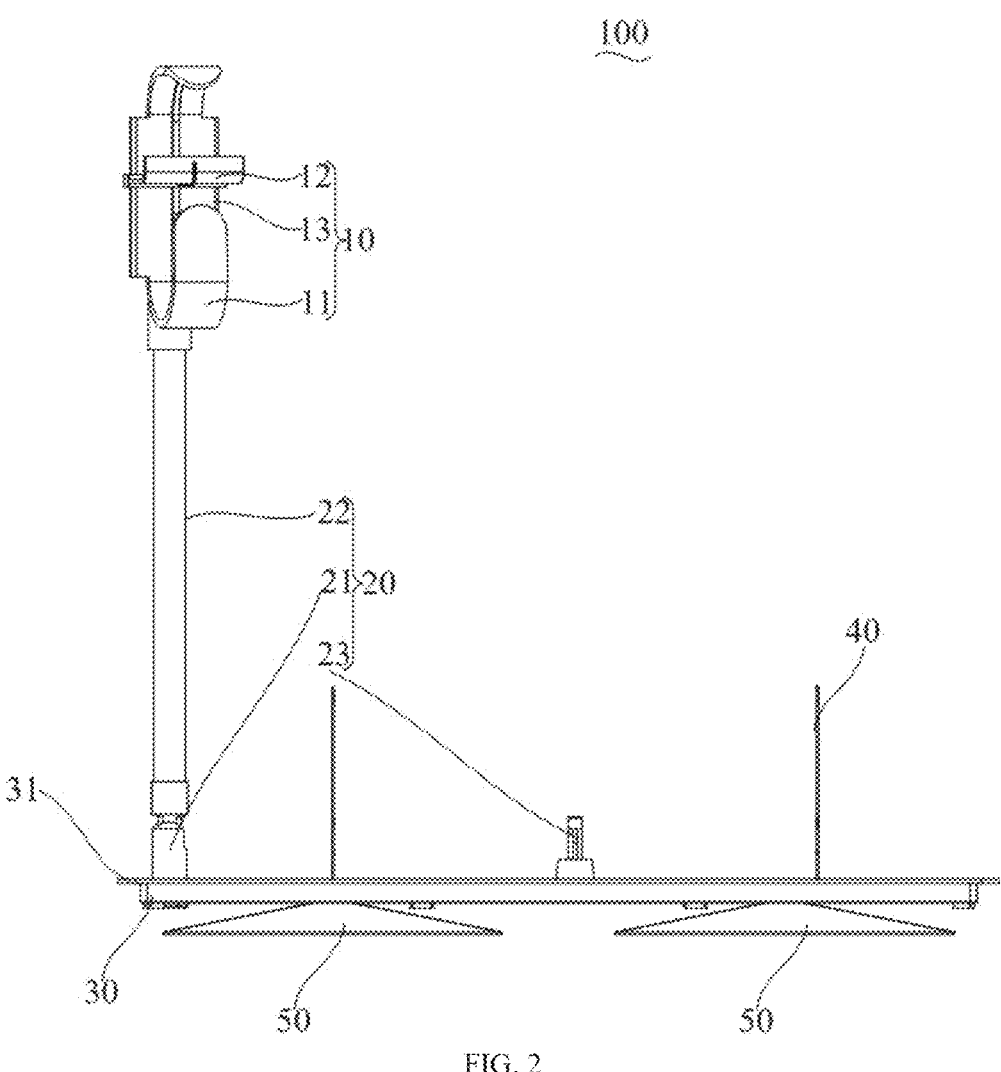
FIG. 2 is a front view of the ventilator support device shown in FIG. 1.
Figure 3:
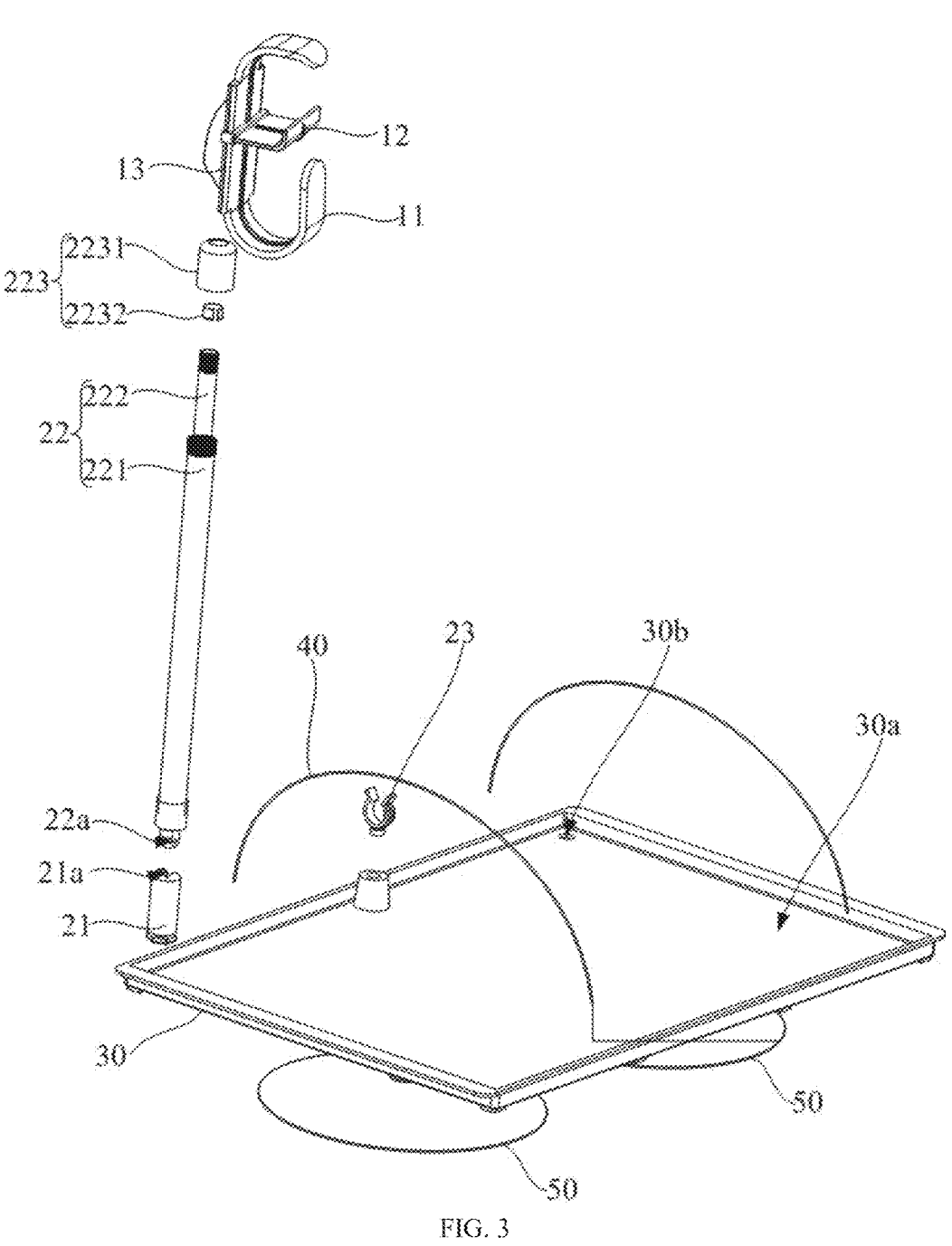
FIG. 3 is an exploded view of the structure of the ventilator support device shown in FIG. 1.
Figure 4:
FIG. 4 is an exploded view of the structure of the gas delivery hose hook in FIG. 1.
Figure 4:

Please refer to FIG. 1 to FIG. 3 again. The present disclosure also provides a ventilator support device 100, which includes a support tray 30, a mounting structure 20 and a gas delivery hose hook 10. The specific structure of the gas delivery hose hook 10 refers to the above-mentioned embodiment. As the ventilator support device 100 adopts all the technical solutions of all the above-mentioned embodiments, it has at least all the beneficial effects brought by the technical solutions of the above-mentioned embodiments, which will not be repeated here. The support tray 30 has a rectangular shell-like structure and is made of metal sheet metal material, and an accommodating groove 30a for placing a ventilator is formed. The mounting structure 20 is detachably connected to the support tray 30, and the gas delivery hose hook 10 is connected to the end of the mounting structure 20 far away from the support tray 30.

It shall be appreciated that because the ventilator needs to continuously add water to its interior during actual use, and distilled water will also be produced during use, it will inevitably lead to water flowing to the desktop or floor during actual work, which will affect the use environment and cause potential safety hazards. Therefore, by arranging the support tray 30 with the accommodating groove 30a, the present disclosure not only facilitates the user to place the ventilator, but also can store the outflow water, thus avoiding potential safety hazards.

Generally speaking, the water tank of the ventilator is arranged on the side of the host machine and adopts a drawer-type push-pull structure. Therefore, in order to avoid interference with the support tray 30 when it is taken and placed, in this application, the groove depth of the accommodating groove 30a should be less than the distance from the bottom of the water tank to the bottom of the host machine, so as to facilitate the user to take and place the water tank.

In this application, the mounting structure 20 includes a connecting seat 21 and a mounting rod 22, wherein the support tray 30 is provided with a plurality of mounting holes 30b, and the connecting seat 21 can be inserted into any mounting hole 30b. The mounting rod 22 is connected to the connecting seat 21, the gas delivery hose hook 10 is connected to the end of the mounting rod 22, and the mounting rod 22 can move relative to the support tray 30, so that the gas delivery hose hook 10 is in a storage state or a use state. That is, when the gas delivery hose hook 10 is in the storage state, the mounting rod 22 and the support tray 30 are placed in parallel, and when in use, the mounting rod 22 and the support tray 30 are placed vertically. By arranging the mounting structure 20, not only can the gas delivery hose hook 10 be fixed above the ventilator, but also it is convenient to use and store. At the same time, by arranging a plurality of mounting holes 30b, it is convenient for users to install the connecting seat 21 and the mounting rod 22 at corresponding positions without rotating the support tray 30, so as to adapt to different working environments.

It shall be appreciated that the mounting hole 30b in this application can be a blind hole or a through hole. When the mounting hole 30b is a through hole, it can be blocked by placing a rubber plug to prevent the water in the accommodating groove 30a from flowing out of the mounting hole 30b.

Please refer to FIG. 3 again. Specifically, the mounting structure 20 includes a mounting shaft (not shown). The connecting seat 21 is provided with a first shaft hole 21a, and the end of the mounting rod 22 is correspondingly provided with a second shaft hole 22a. The mounting shaft penetrates through the first shaft hole 21a and the second shaft hole 22a to connect the mounting rod 22 with the connecting seat 21. In actual use, by rotating the mounting rod 22, the gas delivery hose hook 10 is switched between the use state and the storage state, with simple structure and convenient operation.

Further, the mounting structure 20 also includes a fixing buckle 23, wherein the fixing buckle 23 is connected to the support tray 30 and is located on the rotation path of the mounting rod 22 toward the support tray 30. When the gas delivery hose hook 10 is in a storage state, that is, the mounting rod 22 and the support tray 30 are arranged in parallel, the middle part of the mounting rod 22 is clamped with the fixing buckle 23, and it is fixed with the support tray 30 by the fixing buckle 23, so that the mounting rod 22 and the support tray 30 can be prevented from rotating and separating during the transportation of the ventilator support device 100.

Further, the mounting rod 22 in the present disclosure includes a fixed rod body 221 and a movable rod body 222, wherein the fixed rod body 221 is molded from a metal material and connected to the connecting seat 21 by welding or machining, and the fixed rod body 221 is provided with an insertion hole, the aperture of which is adapted to the rod diameter of the movable rod body 222. The movable rod body 222 can be slidably inserted into the insertion hole, and the end of the fixed rod body 221 is formed with external threads by machining. The gas delivery hose hook 10 is provided with a threaded hole, and the end of the movable rod body 222 is screwed into the threaded hole. Under the action of external force, the movable rod body 222 can slide in the insertion hole, so that the height of the gas delivery hose hook 10 can be adjusted in the use state, so that the ventilator support device 100 can better adapt to different use requirements and has better compatibility.

In an embodiment of the present disclosure, the mounting rod 22 further includes a fixed spring (not shown), and the end of the connecting seat 21 facing the fixed rod body 221 is provided with an arc-shaped clearance groove (not shown) communicating with the first shaft hole 21a, and the fixed spring is elastically installed in the arc-shaped clearance groove. When the connecting seat 21 is rotationally connected with the fixed rod body 221 through the mounting shaft, the fixed spring elastically abuts against the fixed rod body 221 and the connecting seat 21. To some extent, the relative rotation of the fixed rod body 221 and the connecting seat 21 can be avoided through the elastic abutting action of the fixed spring, that is, the position of the gas delivery hose hook 10 in the use state and the storage state is more stable, and the use performance of the ventilator support device 100 is more stable.

Please refer to FIG. 3 again. In this embodiment, the mounting rod 22 further includes a fastener 223, which is connected to the fixed rod body 221 and the movable rod body 222. Specifically, the fastener 223 includes an adjusting nut 2231 and an elastic snap ring 2232, wherein the elastic snap ring 2232 is made of a plastic material and has a cone shape with one side open, that is, the elastic snap ring 2232 is a discontinuous ring in the vertical direction. The elastic snap ring 2232 is sleeved on the outer side of the movable rod body 222, and the adjusting nut 2231 is sleeved on the outer side of the elastic snap ring 2232 and screwed with the fixed rod body 221. In actual use, the adjusting nut 2231 can be rotated to continuously press the elastic snap ring 2232, and the elastic snap ring 2232 elastically abuts against the adjusting nut 2231 and the movable rod body 222 after being contracted, thereby fixing the fixed rod body 221 and the movable rod body 222. By arranging the fastener 223, it is convenient for users to adjust the overall length of the mounting rod 22.

In an embodiment of the present disclosure, the ventilator support device 100 further includes an elastic fixing rope 40, one end of which is connected to one side of the support tray 30, and the other end is connected with a fixing hook (not shown), and the other side of the support tray 30 is provided with a fixing hole adapted to the fixing hook. When the ventilator is placed in the accommodating groove 30a, the elastic fixing rope 40 of the fixing hook is buckled in the fixing hole, and the elastic fixing rope 40 is pressed on the surface of the host machine. According to the application, the host machine can be stably pressed in the accommodating groove 30a through the elastic action of the elastic fixing rope 40.

Further, the support tray 30 of the present disclosure also includes a booster flange 31, which can be formed by the support tray 30 through a bending process, and the booster flange 31 is connected to two opposite sides of the support tray 30, which can greatly facilitate the user to transfer the ventilator and the ventilator support device 100 as a whole.

In an embodiment of the present disclosure, the ventilator support device 100 further includes a fixed suction cup 50, which is made of elastic silicone rubber material and connected to the bottom of the support tray 30 by glue or screw structure. The number and size of the fixed suction cups 50 can be set according to actual needs, and the support tray 30 can be placed on the workbench more stably through the vacuum adsorption of the fixed suction cups 50.

The present disclosure also provides respiratory therapy equipment (not shown), which includes a ventilator (not shown) and a ventilator support device 100. The specific structure of the ventilator support device 100 refers to the above-mentioned embodiment. Because the respiratory therapy equipment adopts all the technical solutions of all the above-mentioned embodiments, it has at least all the beneficial effects brought by the technical solutions of the above-mentioned embodiments, so I will not repeat them here. The ventilator includes a host machine and a gas delivery hose 200 connected to the host machine. The ventilator support device 100 includes a support tray 30, a mounting structure 20 and a gas delivery hose hook 10. The support tray 30 is formed with an accommodating groove 30a, and the host machine part is accommodated in the accommodating groove 30a. The mounting structure 20 is detachably connected to the support tray 30. The gas delivery hose hook 10 is connected to the end of the mounting structure 20 far from the support tray 30, and the gas delivery hose hook 10 is wound around the gas delivery hose.

The above is only the preferred embodiment of the present disclosure, which does not limit the patent scope of the present disclosure. Any equivalent structural transformation made by using the description and attached drawings of the present disclosure or direct/indirect application in other related technical fields under the inventive concept of the present disclosure shall be included in the patent protection scope of the present disclosure.

What is claimed is:

1. A gas delivery hose hook applied to a gas delivery hose, wherein a surface of the gas delivery hose is provided with a plurality of grooves which are arranged at intervals along a length direction of the gas delivery hose; wherein the gas delivery hose hook comprises: a body; a first hook body connected to the body and provided with a first limit rib, wherein the first limit rib extends along an extending direction of the first hook body; at least one second hook body is connected to the body and arranged at intervals with the first hook body, wherein two opposite surfaces of the second hook body are convexly provided with second limit ribs; wherein the gas delivery hose is wound around the first hook body and the second hook body, and the first limit rib and the second limit ribs can be embedded in any of the plurality of grooves; wherein two opposite sides of the second hook body are provided with sliding mounting grooves; and wherein the body comprises a mounting plate and an elastic anti-slip layer; the first hook body and the second hook body are connected to the mounting plate, the elastic anti-slip layer is connected to two opposite sides of the mounting plate and extends along a length direction thereof; and the elastic anti-slip layer elastically abuts against groove side walls of the sliding mounting grooves.

2. The gas delivery hose hook according to claim 1, wherein a cross section of the first limit rib and the second limit ribs are rectangular.

3. The gas delivery hose hook according to claim 1, wherein the body comprising edges embedded in the sliding mounting grooves, and the second hook body can reciprocate relative to the first hook body.

4. The gas delivery hose hook according to claim 1, wherein the second hook body comprises a mounting seat and a hook plate, and the mounting seat is provided with the sliding mounting grooves; the second limit ribs are arranged at two opposite sides of the hook plate, and the hook plate is detachably connected to the mounting seat.

5. The gas delivery hose hook according to claim 4, wherein the mounting seat is provided with a clamping groove, the clamping groove penetrates through two opposite side surfaces of the mounting seat, and the hook plate is slidably embedded in the clamping groove.

6. The gas delivery hose hook according to claim 1, wherein the gas delivery hose hook comprises a plurality of second hook bodies, and the plurality of second hook bodies are connected to the body and arranged at intervals with the first hook body.

7. A ventilator support device, comprising a support tray, a mounting structure and a gas delivery hose hook, wherein the gas delivery hose hook is the gas delivery hose hook according to claim 1;

the support tray is formed with an accommodating groove configured to accommodate a ventilator, the mounting structure is detachably connected to the support tray, and the gas delivery hose hook is connected to an end of the mounting structure far away from the support tray.

8. The ventilator support device according to claim 7, wherein the mounting structure comprises a connecting seat and a mounting rod; the support tray is provided with a plurality of mounting holes, and the connecting seat can be inserted into any of the mounting holes; the mounting rod is connected to the connecting seat, and the gas delivery hose hook is connected to an end of the mounting rod; and the mounting rod can move relative to the support tray, so that the gas delivery hose hook can be in a storage state or a use state.

9. The ventilator support device according to claim 8, wherein the connecting seat is provided with a first shaft hole, and the mounting rod is provided with a second shaft hole.

10. The ventilator support device according to claim 8, wherein the mounting structure further comprises a fixed buckle, which is connected to the support tray; when the gas delivery hose hook is in the storage state, a middle part of the mounting rod is clamped with the fixed buckle.

11. The ventilator support device according to claim 8, wherein the mounting rod comprises a fixed rod body and a movable rod body; the fixed rod body is connected to the connecting seat and is provided with an insertion hole, and the movable rod body is slidably inserted into the insertion hole; and the gas delivery hose hook is connected to an end of the movable rod body.

12. The ventilator support device according to claim 11, wherein the mounting rod further comprises a fastener, and the fastener is connected to the fixed rod body and the movable rod body.

13. The ventilator support device according to claim 12, wherein the fastener comprises an adjusting nut and an elastic snap ring, the elastic snap ring is sleeved outside the movable rod body, and the adjusting nut is sleeved outside the elastic snap ring and is in threaded connection with the fixed rod body; the adjusting nut rotates relative to the fixed rod body so that the elastic snap ring elastically abuts against the adjusting nut and the movable rod body.

14. The ventilator support device according to claim 11, wherein the ventilator support device further comprises an elastic fixing rope, one end of which is connected to one side of the support tray, and the other end of which is detachably connected to the other side of the support tray, so as to press the ventilator in the accommodating groove.

15. The ventilator support device according to claim 7, wherein the support tray further comprises a booster flange, and the booster flange is connected to two opposite sides of the support tray.

16. The ventilator support device according to claim 7, wherein the ventilator support device further comprises a fixed suction cup, and the fixed suction cup is connected to the bottom of the support tray.

17. A gas delivery hose hook applied to a gas delivery hose, wherein a surface of the gas delivery hose is provided with a plurality of grooves which are arranged at intervals along a length direction of the gas delivery hose; wherein the gas delivery hose hook comprises: a body; a first hook body connected to the body and provided with a first limit rib, wherein the first limit rib is formed on an inner side of the first hook body, extends along an extending direction of the first hook body, and further extends toward an upper side of the body; at least one second hook body is connected to the body and arranged at intervals with the first hook body, wherein two opposite surfaces of the second hook body are convexly provided with second limit ribs; wherein the second hook body is provided with a vertical groove on a horizontal axis of the second hook body facing the body; wherein the vertical groove is configured to correspond to the first limit rib to enable stable engagement between the second hook body and the body; and wherein the gas delivery hose is wound around the first hook body and the second hook body, and the first limit rib and the second limit ribs are configured to be embedded in any of the plurality grooves.

* * * * *